United States Patent [19]
Tani et al.

[11] Patent Number: 6,164,933
[45] Date of Patent: Dec. 26, 2000

[54] METHOD OF MEASURING A PRESSURE OF A PRESSURIZED FLUID FED THROUGH A DIAPHRAGM PUMP AND ACCUMULATED IN A VESSEL, AND MINIATURE PUMP SYSTEM EFFECTING THE MEASUREMENT

[75] Inventors: Michihiko Tani, Sanda; Yasufumi Masaki, Hirakata, both of Japan

[73] Assignee: Matsushita Electric Works, Ltd., Osaka, Japan

[21] Appl. No.: 09/298,856

[22] Filed: Apr. 26, 1999

[30] Foreign Application Priority Data

| Apr. 27, 1998 | [JP] | Japan | 10-116355 |
| Dec. 4, 1998 | [JP] | Japan | 10-345801 |

[51] Int. Cl.$^7$ .................................................. F04B 17/00
[52] U.S. Cl. ........................... 417/413.2; 417/413.3; 417/53; 417/440; 73/168
[58] Field of Search .................... 417/413.2, 413.3, 417/53, 297, 439, 440; 73/168

[56] References Cited

U.S. PATENT DOCUMENTS

| 3,963,380 | 6/1976 | Thomas, Jr. et al. | 417/322 |
| 4,583,917 | 4/1986 | Shah | 417/63 |
| 4,697,989 | 10/1987 | Perlov et al. | 417/53 |
| 5,047,950 | 9/1991 | Fritsch et al. | 364/510 |
| 5,239,319 | 8/1993 | Miyazaki et al. | 340/679 |
| 5,240,008 | 8/1993 | Newell | 128/685 |
| 5,271,724 | 12/1993 | Van Lintel | 417/413 |
| 5,466,932 | 11/1995 | Young et al. | 250/289 |

*Primary Examiner*—Timothy S. Thorpe
*Assistant Examiner*—Timothy P. Solak
*Attorney, Agent, or Firm*—Arent Fox Kinter Plotkin & Khan, PLLC

[57] ABSTRACT

A method and system for determination of a pressure of the pressurized fluid with the use of a diaphragm pump responsible for accumulating the pressurized fluid in the vessel. The pump has a pump cavity and a diaphragm with a piezoelectric element which is actuated by an application of a voltage to displace the diaphragm for pumping a fluid into the vessel. The method comprises the steps of:

(a) deactivating the diaphragm by removal of the voltage to the piezoelectric element so as to stop pumping the fluid and accumulating the pressurized fluid into the vessel;

(b) introducing the pressurized fluid only from the vessel back into the pump cavity so as to cause a displacement of the diaphragm by the pressurized fluid;

(c) deriving an electrical signal indicative of the displacement of the diaphragm; and (d) translating the electrical signal into a corresponding pressure value indicative of the pressure of the pressurized fluid in the vessel.

20 Claims, 11 Drawing Sheets

METHOD OF MEASURING A PRESSURE OF A PRESSURIZED FLUID FED THROUGH A DIAPHRAGM PUMP AND ACCUMULATED IN A VESSEL, AND MINIATURE PUMP SYSTEM EFFECTING THE MEASUREMENT

BACKGROUND OF THE INVENTION

1. Field of the Invention

The present invention is directed to a method of measuring a pressure of a pressurized fluid fed through a diaphragm pump and accumulated in a vessel, and a miniature pump system for in situ measurement of the pressure within the pump.

2. Description of the Prior Art

Diaphragm pumps are well known in the art. Specifically, the pump utilizing a piezoelectric element for actuating a diaphragm has been proposed for miniaturization of the pump. When sensing the pressure of a pressurized fluid developed by the pump and accumulated in a vessel, a separate pressure sensor needs to be provided on the side of the vessel. However, the addition of the separate pressure sensor in or around the vessel gives an additional bulk to a pump system, which is a hindrance to a miniaturization of the pump system.

SUMMARY OF THE INVENTION

The present invention has been achieved in view of the above problem, and has therefore a primary object of providing a method and a system which are capable of measuring the pressure of a pressurized fluid fed through a diaphragm pump and accumulated in a vessel, while eliminating a necessity of providing an additional pressure sensor on the side of the vessel.

The present invention utilizes the diaphragm pump having a pump cavity and a diaphragm with a piezoelectric element which is actuated by an application of a voltage to displace the diaphragm for pumping a fluid into the vessel. The method of the present invention comprises the steps of:

(a) deenergizing the diaphragm by removal of the voltage to the piezoelectric element so as to stop pumping the fluid and accumulating the pressurized fluid into the vessel;

(b) introducing the pressurized fluid only from the vessel back into the pump cavity so as to cause a displacement of the diaphragm by the pressurized fluid;

(c) deriving an electrical signal indicative of the displacement of the diaphragm; and (d) translating the electrical signal into a corresponding pressure value indicative of the pressure of the pressurized fluid in the vessel.

Thus, a target pressure of the pressurized fluid can be obtained with the use of the diaphragm pump as a sensing device, eliminating the necessity of an additional pressure sensor on the side of the vessel.

Preferably, the electrical signal is a voltage which is developed at the piezoelectric element as a result of the piezoelectric element being stressed by the displacement of the diaphragm under the effect of the pressurized fluid introduced into the pump cavity back from the vessel. With this arrangement, the piezoelectric element is utilized both as an actuator of the diaphragm and as a pressure sensor, thereby reducing the number of the parts of the pump system for miniaturization of the system. In this system, the voltage developed at the piezoelectric element may be integrated over a predetermined time period to give an integrated voltage for determination of the pressure value.

Alternately, the electrical signal may originate from static capacitance which is developed between a fixed sensor electrode and a movable electrode on the diaphragm. The capacitance will vary in response to the displacement of the diaphragm under the effect of the pressurized fluid introduced into the pump cavity back from the vessel.

Further, it is equally possible to use a piezoelectric resistor on the diaphragm which develops a resistance varying in response to the displacement of the diaphragm. The resistance variation is processed for determination of the pressure value of the pressurized fluid.

The pump system of the present invention includes a pump and a return means which allows the pressurized fluid to return into the pump cavity from the vessel. A controller is included to provide a measurement cycle and deenergize, within the measurement cycle, the piezoelectric element to stop actuating the diaphragm while at the same time activates the return means to introduce the pressurized fluid into the pump cavity back from the vessel for displacing the diaphragm by the pressurized fluid thus introduced. Also included in the system is a processing means which derives an electrical signal caused by the displacement of the diaphragm within the measurement cycle and translates the electrical signal into a corresponding pressure value indicative of the pressure of the pressurized fluid in the vessel.

When the electrical signal is the voltage developed at the piezoelectric element as a result of the diaphragm being stressed due to its displacement by the pressurized fluid, the piezoelectric element is preferred to have a composite structure composed of first and second piezoelectric materials of different characteristics. The first piezoelectric material is selected to have a good response sensitivity as an actuator for displacing the diaphragm and the second piezoelectric material is selected to have a good response sensitivity as a sensor for the displacement of the diaphragm. To this end, the first piezoelectric material has a greater piezoelectric strain constant (d33) and a smaller voltage output constant (g33) than the second piezoelectric material.

The diaphragm may carry a movable sensor electrode which displaces together with the diaphragm and is opposed to a fixed sensor electrode to vary a static capacitance between the movable and fixed sensor electrodes for determination of the pressure value. In this version, the diaphragm is of a planar configuration and is supported at its periphery to a casing of the pump around the pump cavity so as to have a center movable part responsible for pumping action and a peripheral stationary part. The movable sensor electrode extends over substantially the entire area of one face of the diaphragm with a dielectric layer interposed therebetween. The fixed sensor electrode is also of a planar configuration and fixed to the casing to form a gap with the movable sensor electrode.

The piezoelectric element may be provided separately from the diaphragm to displace the diaphragm. In this instance, the diaphragm of a planar configuration carries at its periphery an annulus of the piezoelectric element by which the diaphragm is supported to a casing of the pump around the pump cavity. The piezoelectric element drives upon being applied a voltage to displace the diaphragm substantially linearly in a direction of varying a gap between the movable and fixed sensor electrodes while varying a volume of the pump cavity. The movable electrode extending over substantially the entire area of one face of the diaphragm opposes the fixed sensor electrode also of a planar configuration fixed to the casing so as to give a varying static capacitance in correspondence to the displacement of the diaphragm for detection of the pressure of the pressurized fluid. For the piezoelectric element which actuates the diaphragm substantially linearly, it is preferred to use the piezoelectric element in the form of a laminate of layers of piezoelectric material which are connected in parallel with each other across a driving voltage source.

As an alternative to the electrical signal originating from the voltage or from the static capacitance, it is equally possible to use the electrical signal originating from a piezoelectric resistor network deposited on the diaphragm. In response to the displacement or deformation of the diaphragm, the piezoelectric resistor network exhibits a varying resistance which is processed for determination of the pressure value.

In a preferred embodiment, the pump operates to feed an air to accumulate a pressurized air in the vessel and is provided with an active release valve which is capable of opening the pump cavity to an atmospheric pressure. The control means actuates the release valve to open immediately before activating the return means to introduce the pressurized air into the pump cavity back from the vessel, thereby eliminating a back pressure remaining in the pump prior to measuring the pressure of the pressurized air for reliable and accurate measurement thereof.

Inlet and outlet valves of the pump provided respectively for drawing an outside air into the pump and feeding the air into the vessel are preferred to be of a microstructure having a valve opening of not more than 0.5 mm in diameter and operating at an opening/closing rate of not more than 0.1 sec. Each of the inlet and outlet valves may be driven to operate by a piezoelectric actuator in synchronous with the actuation of the diaphragm by the piezoelectric element for improved response sensitivity in the pressure measurement.

The above pump system with the in situ pressure measurement capability is best utilized for a blood pressure measuring device in which the vessel is presented as a cuff for occluding an artery of a human body. For this purpose, the processing means further includes a pulse wave detection means which monitors a pulse wave occurring in the pressurized air within the measurement cycle so as to detect an appearance of systole and diastole and to provide systole and diastole signals respectively at the detection of the systole and diastole. The processing means allocates the pressure value to the systole and diastole signals for giving the systolic and diastolic pressures.

These and still other objects and advantageous features of the present invention will become more apparent from the following description of the embodiments when taken in conjunction with the attached drawings.

DETAILED DESCRIPTION OF THE EMBODIMENTS

Figure 1:
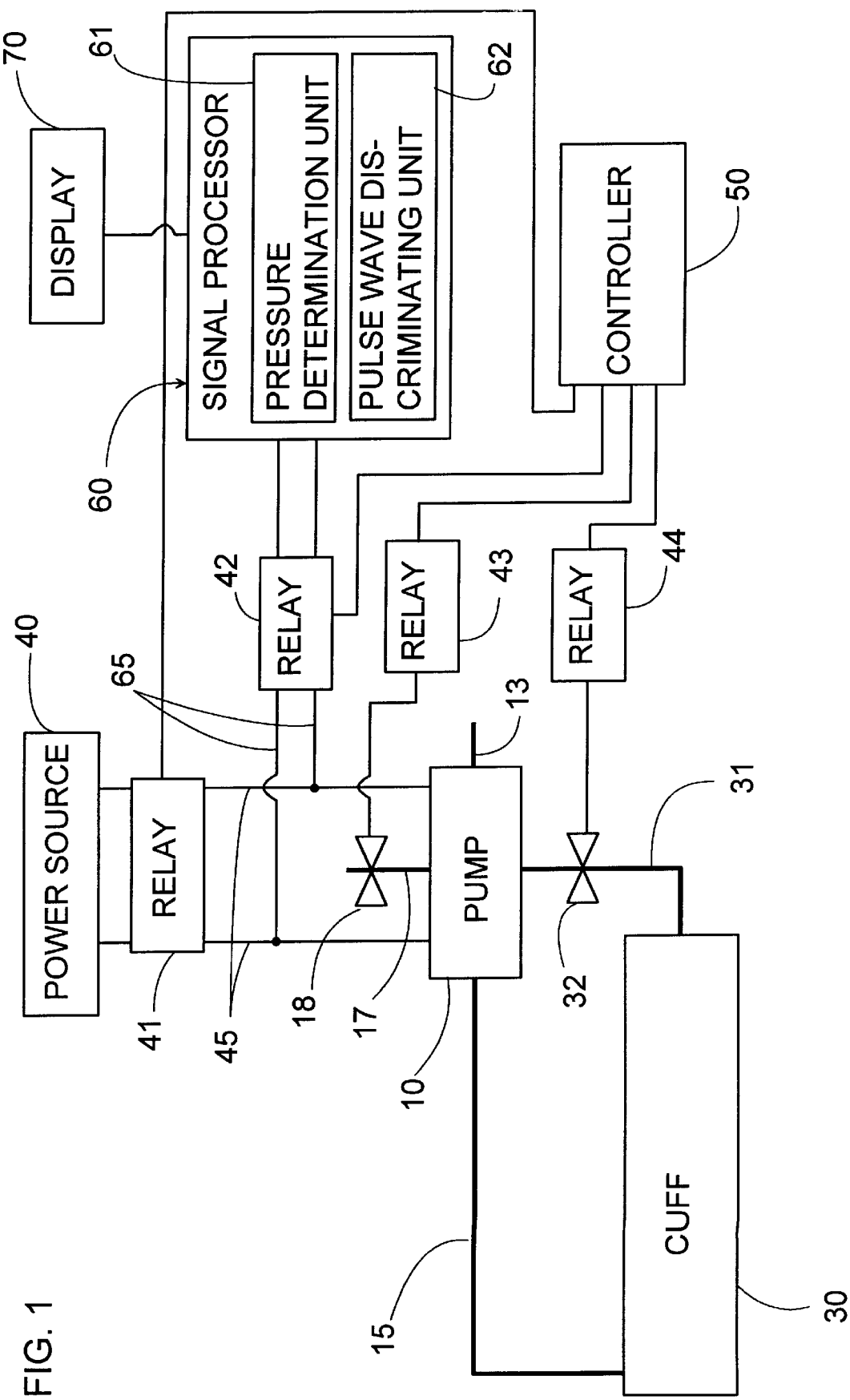
FIG. 1 is a block diagram of a pump system in accordance with a first embodiment of the present invention.
Figure 2:
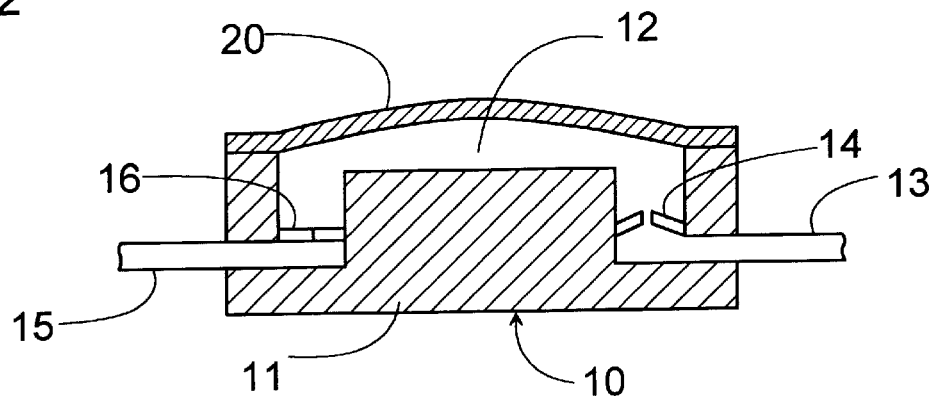
FIGS. 2 and 3 are schematic views illustrating an operation of a diaphragm pump utilized in the above system.
Figure 3:
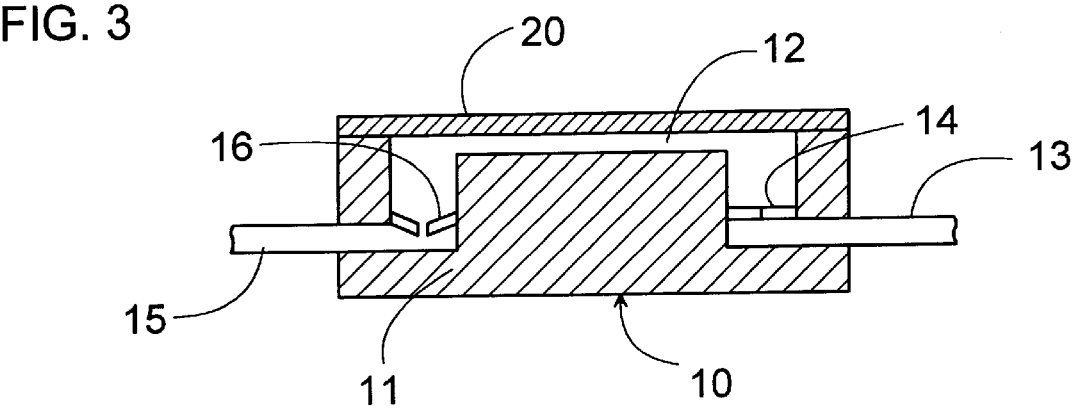
Figure 4:
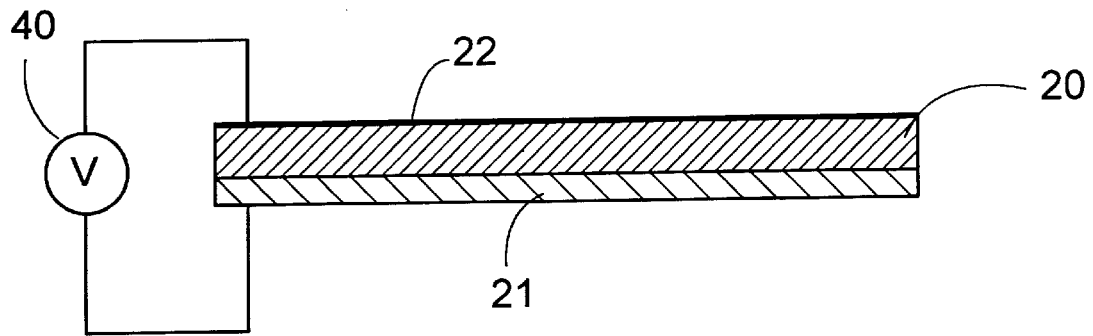
FIG. 4 is a sectional view of a diaphragm of the above pump.

Referring now to FIGS. 1 to 4, there is shown a pump system in accordance with a first embodiment of the present invention. The pump system is adapted for measurement of a blood pressure and includes a diaphragm pump 10, a cuff 30 for occluding an artery of a human body, and an electronics for controlling the pump. The pump 10 draws in an outside air through an inlet path 13 and feed it through an outlet path 15 to accumulate a pressurized air in the cuff 30 or vessel. As shown in FIGS. 2 to 4, the pump 10 has a diaphragm 20 which is made of a piezoelectric element, for example, PZT and defines a pump cavity 12 between the pump casing 11 and the diaphragm. The diaphragm 20 is formed on opposite faces thereof with driving electrodes 21 and 22. A power source 40 is connected to apply a DC pulse voltage through a relay 41 across the electrodes 21 and 22, causing the diaphragm to deflect or displace repeatedly, thereby drawing the air through an inlet valve 14 and feeding it to the cuff through an outlet valve 16. As usual with the known diaphragm pump, the inlet and outlet valves are of passive type and operate respectively only for drawing the air into the pump cavity 12 and only for discharging the air from the cavity.

The pump is fabricated partly by a LIGA process or the like process into a miniature structure with the diaphragm 20 being supported at its periphery to a pump casing 11 so that a remaining center portion of the diaphragm is responsible for the pumping action. The thickness of the electrodes 21 and 22 are selected to facilitate the deflection of the diaphragm. For example, the lower electrodes 21 and the upper electrode 22 are selected to have thickness of 0.1 mm and 0.01 mm, respectively for the PZT diaphragm of 0.25 mm thickness.

The cuff 30 is connected to the pump through a return path 31 in order to introduce the pressurized air into the pump cavity 12 back from the cuff for measurement of the pressurized air by use of the diaphragm 20. A return valve 32 is disposed in the return path 31 and is actuated through a relay 44 by a controller 50. Extending from the pump cavity 12 is a release path 17 with a release valve 18 for evacuating the air prior to introducing the pressurized air from the cuff 30 back into the pump cavity 12, as will be discussed later. The release valve 18 is controlled to open and close by the controller 50 through a relay 43. A signal processor 60 is connected in circuit to determine the pressure of the pressurized air introduced into the pump cavity 12 from the cuff 30 based upon the displacement of the diaphragm 20 caused by the pressurized air. For this purpose, a signal line 65 diverges from a drive line 45 of applying the DC pulse voltage across the driving electrodes 21 and 22 and extends to the signal processor 60 through a relay 42 so that a voltage developed as a result of the diaphragm being deformed is fed to the signal processor 60. Relays 41 and 42 are also controlled by the controller 50 in such a manner as to drive the pump 10 for accumulating the pressurized air in the cuff 30 and deenergize the pump 10 for taking the voltage from the diaphragm 20, selectively.

The signal processor 60 includes a pressure determination unit 61 responsible for determination of the pressure of the pressurized air and a pulse wave discriminating unit 62 for judging particular timings at which systole and diastole appear based upon a pulse wave occurring in the pressurized air within the cuff for determination of systolic and diastolic pressures. The determination of the pressure and the appearances of the systole and diastole are both judged from a variation in the voltage developed at the diaphragm 20 itself, i.e., the piezoelectric element. The systolic and diastolic pressures determined by the signal processor 60 are indicated at a display 70.

Figure 5:
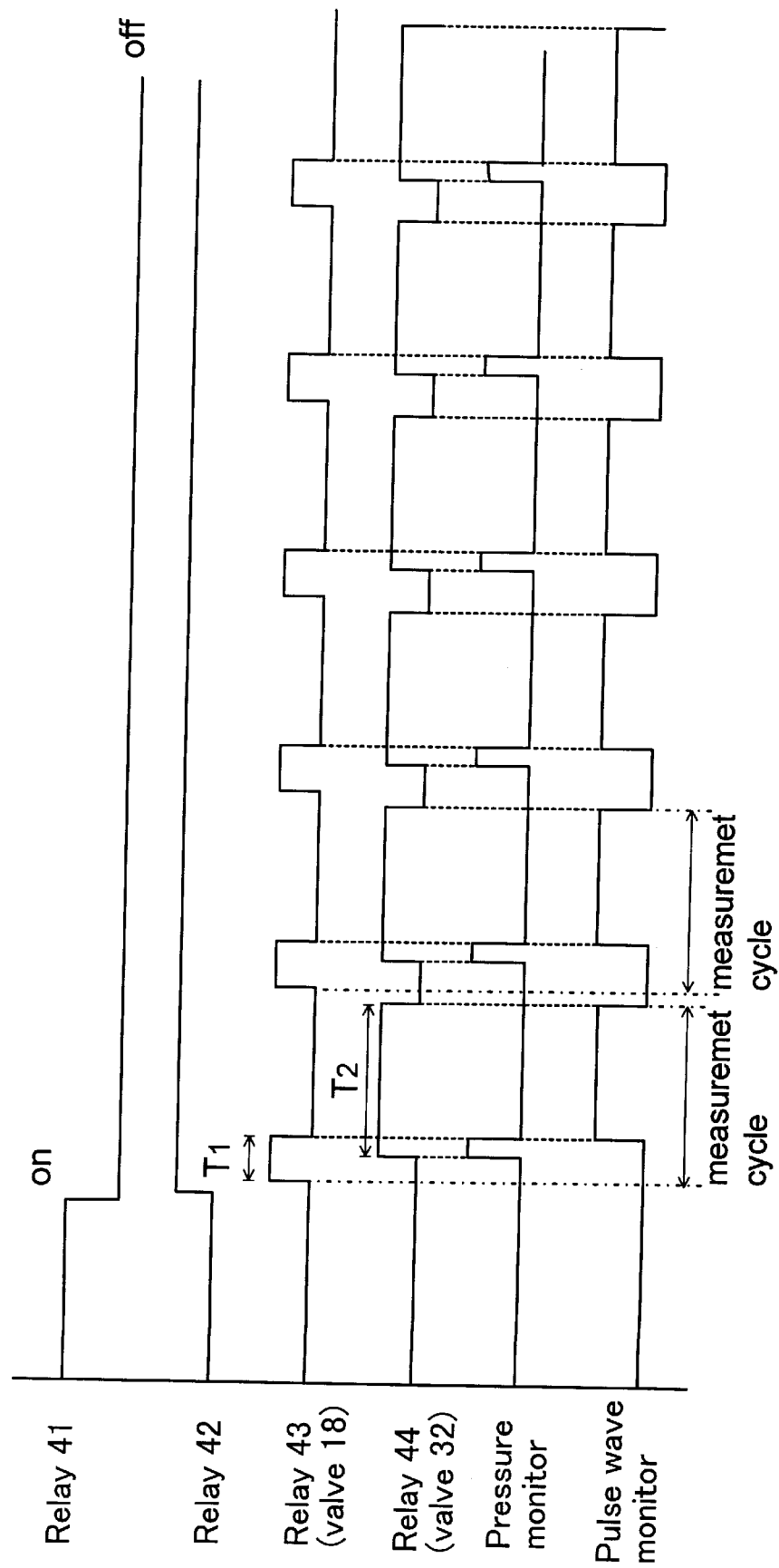
FIG. 5 is a timing chart illustrating one mode for a blood pressure measurement with the use of the pump system.

Operation of the system is discussed with reference to FIG. 5, which illustrates one mode for determination of the systolic and diastolic pressures during the course of lowering the pressure of the cuff 30. After the cuff 30 has been inflated to reach a sufficient pressure level, the controller 50 deenergizes relay 41 to stop providing the driving voltage to the diaphragm 20, and energize relay 42 so that the signal processor 60 is ready for receiving a voltage from the diaphragm 20, i.e., piezoelectric element. Then, the controller 50 gives a number of measurement cycles within each of which an instant pressure of the cuff 30 is determined and the appearance of the systole or diastole is checked. The sufficient pressure level is determined by periodically providing like measurement cycles for determination of the cuff pressure during the course of inflating the cuff 30, or by estimation of the cuff pressure in terms of a time elapsed for inflating the cuff. Each measurement cycle during the course of lowering the cuff pressure begins to energize relay 43 for a short time period T1 to open release valve 18 for discharging a pressurized air remaining in the pump cavity 12, i.e., releasing back pressure in the cavity. Before closing release valve 18, return valve 32 is opened to introduce the pressurized air from the cuff 30 back into the pump cavity 12, thereby deforming the diaphragm 20 by the pressurized air to generate a corresponding voltage at the piezoelectric element. The voltage appears across the electrodes 21 and 22 and is fed through the signal line 65 to the signal processor 60. Return valve 32 is kept opened by relay 44 for a time period T2 within which the pressure determination unit 61 is first to determine the cuff pressure and subsequently the pulse wave discriminating unit 62 operates to judge the appearances of the systole and diastole. The measurement cycle terminates at the end of the time period T2.

Figure 6:
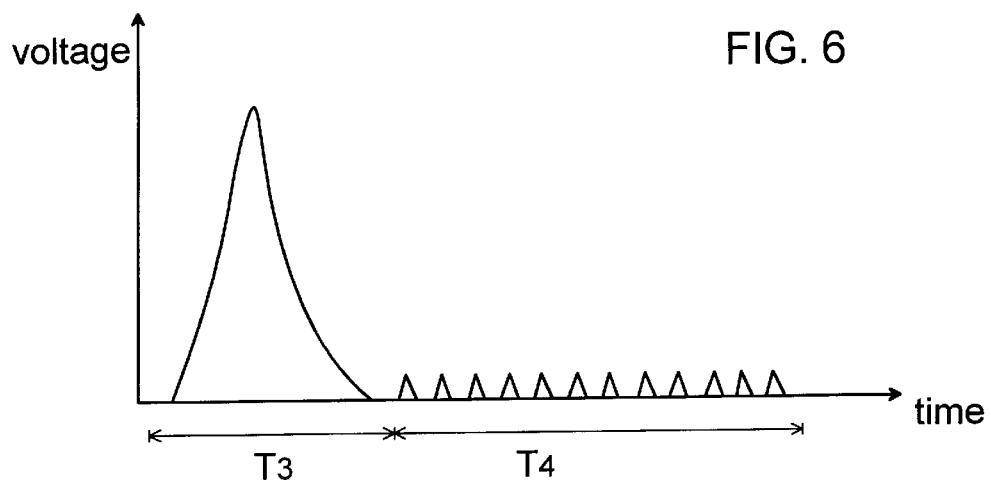
FIGS. 6 to 8 are graphs illustrating the operation of the pump.

As shown in FIG. 6, the voltage from the diaphragm 20 change rapidly to a large extent in the beginning of time period T2 where the pressurized air rushes into the pump cavity from the cuff. This voltage change is analyzed in pressure determination unit 61 to determine a pressure level of the cuff pressure in consideration of relevant factors such as pressure loss in the return path 31. The determination of the cuff pressure may be based upon a peak value of the voltage or an integral of the voltage within a time period T3. The resulting cuff pressure is indicated on the display 70. After closing the release valve 18 at the end of T1, the voltage lowers but represents a minute pulse wave indicative of pulsatile changes in the cuff pressure over a time period T4, as shown in FIG. 6. This voltage variation is analyzed in the pulse wave discriminating unit 62 to judge the appearance of the systole and diastole. The judgement is based upon the voltage level. For example, during the course of repeating measurement cycles, the unit 62 judges the appearance of systole when the minute voltage is first to exceed a systolic reference level, and judges the appearance of diastole when the voltage lowers below a diastole reference level. Upon judgement of the appearance of the systole and diastole, the unit 62 issues systole and diastole signals, respectively, in response to which the processor 60 allocates the instant cuff pressures which are indicated on the display 70 as representing the systolic and diastolic pressures. After the diastolic pressure is determined, the measurement cycles are terminated.

Figure 7:
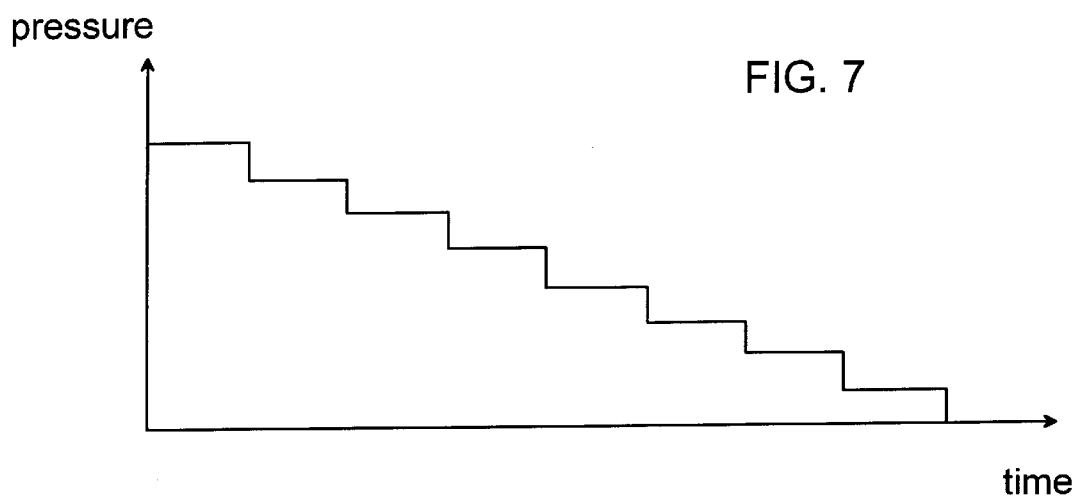

Each of the valves 18 and 32 is preferred to be of a microstructure having a valve opening of 0.5 mm diameter or less and operating at an opening/closing time of 0.1 sec or less. Particularly, with the use of such microstructure valve as the release valve 18, the cuff pressure can be lowered by a less extent in each measurement cycle, as shown in FIG. 7, thereby providing a large number of the measurement cycles during the course of evacuating the cuff, and therefore assuring accurate measurement of the systolic and diastolic pressures.

Figure 8:
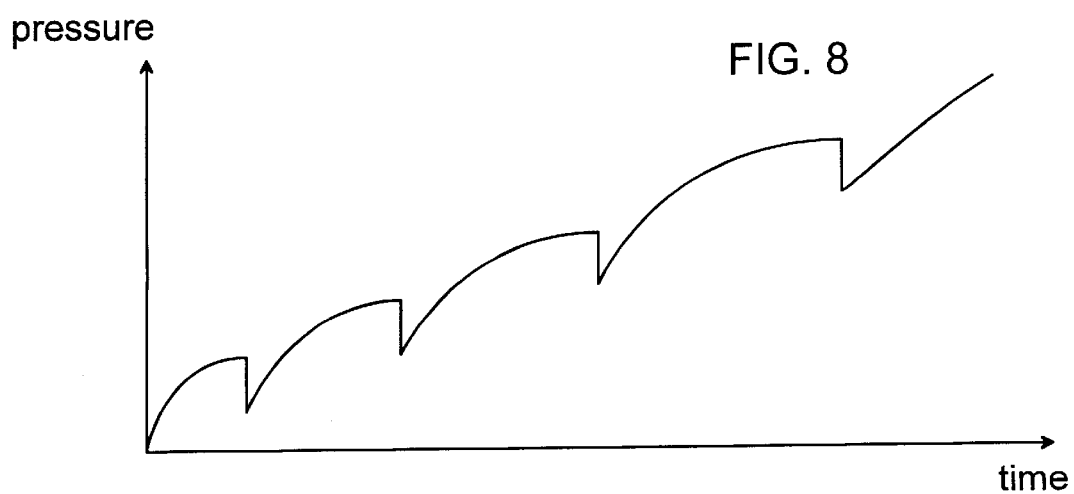
Figure 9:
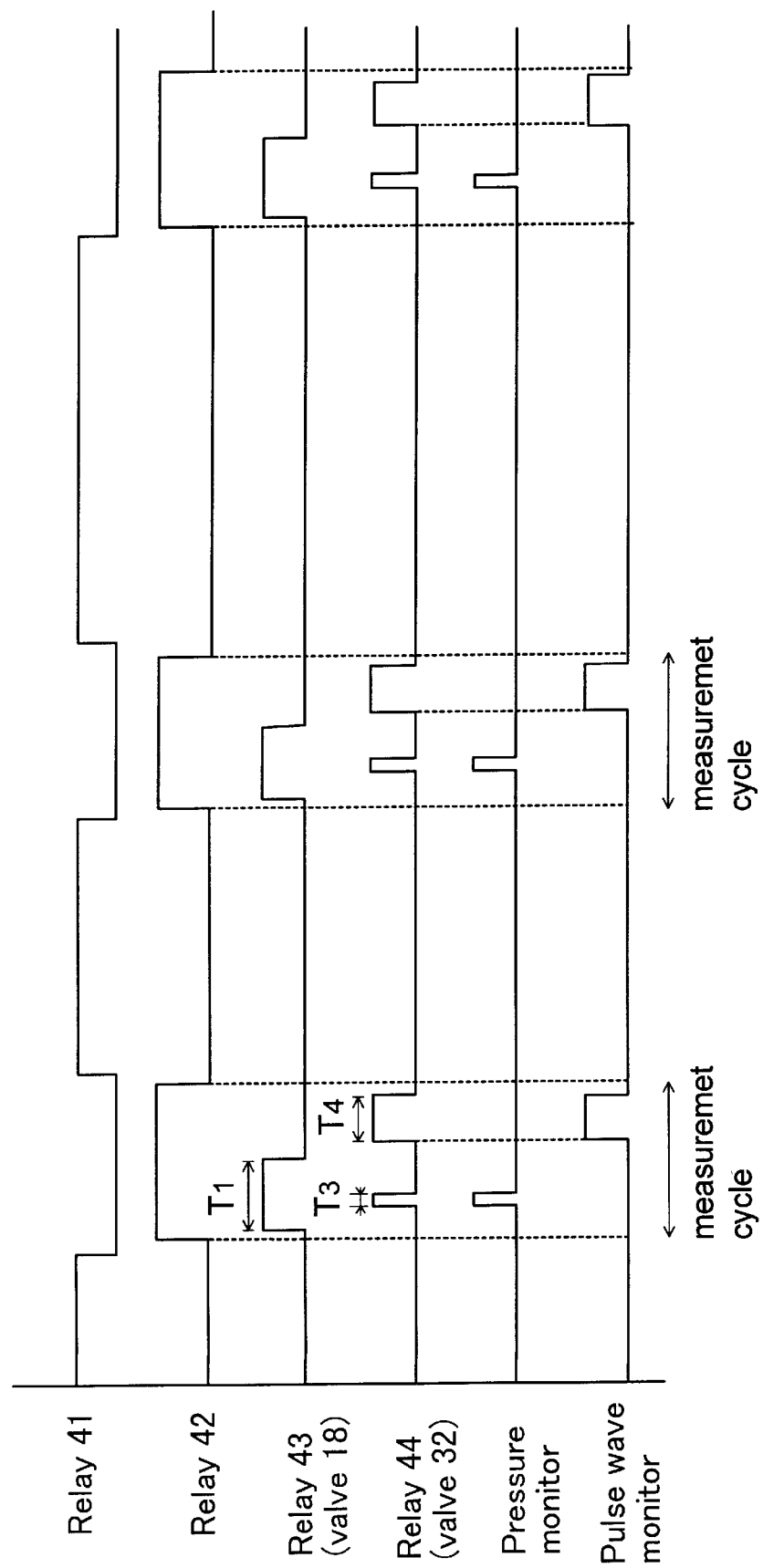
FIG. 9 is a timing chart illustrating another mode for a blood pressure measurement with the use of the pump system.

The same is true when determining the systolic and diastolic pressure in the course of increasing the cuff pressure. That is, as shown in FIG. 8, the cuff can be rapidly inflated while repeating the like measurement cycles associated with the lowering of the cuff pressure. FIG. 9 illustrates this mode of determining the systolic and diastolic pressures while inflating the cuff. The relay 41 is periodically energized to drive the pump 10 intermittently to increase the cuff pressure while defining a number of the measurement cycles in the course of inflating the cuff. In each measurement cycle where the relay 42 is energized to make the processor 60 ready for receiving the voltage from the diaphragm 20, the relay 43 is energized firstly for a time period T1 to remove the back pressure of the pump cavity. Within this time period T1, the return valve 32 is caused to open for a short time period T3 to introduce the pressurized air from the cuff 30, deforming the diaphragm, i.e., the piezoelectric element with attendant voltage developed thereat. The resulting voltage is received at the pressure determination unit 61 where it is processed to determine the instant cuff pressure. Immediately after closing the release valve 18, the return valve 32 is again opened for another short period T4 to monitor the voltage in the form of the pulse wave from the piezoelectric element for determination of the diastole or systole at the unit 62. The appearance of the diastole is acknowledged when the voltage level firstly exceeds a predetermined diastolic reference, and the appearance of the systole is acknowledge when the voltage level goes finally below a predetermined systolic reference over the number of the measurement cycles. In the like manner as in the previous mode, the processor 60 allocates the instant cuff pressures to the appearance of the diastole and systole for indication of the diastolic and systolic pressures respectively on the display 70. This mode terminates when the systolic pressure is finally determined, whereby the controller responds to stop energizing the pump and the electronics. As is apparent from FIGS. 8 and 9, the pump 10 is energized step by step with increasing periods of driving the pump for measurement of the diastolic and systolic pressures while inflating the cuff.

In order to give a good response sensitivity both in actuating the diaphragm and also in sensing the deformation of the diaphragm, the diaphragm is preferred to have a composite piezoelectric structure composed of PZT and PVDF polymer which have different piezoelectric characteristics. PZT is selected to have a good response sensitivity as the actuator for driving the diaphragm and has a great piezoelectric strain constant (d33) of $400\times10^{-12}$ C/N attendant with a small voltage output constant (g33) of $20\times10^{-3}$ mV/N. PVDF is selected to have a good response sensitivity as a sensor for the displacement of the diaphragm and has a great voltage output constant (g33) of $160\times10^{-3}$ omV/N but attendant with a small piezoelectric strain constant (d33) of $20\times10^{-12}$ C/N. The PZT cermamic particles are dispersed in a matrix of PVDF resin to give an overall piezoelectric strain constant (d33) of $300\times10^{-12}$ C/N and an overall voltage output constant (g33) of $80\times10^{-3}$ mV/N. These values are found satisfactory for assuring good sensitivity to the diaphragm both in actuating the pump and sensing the cuff pressure. The characteristics of the composite piezoelectric element can be suitably adjusted by varying blending proportion of the PZT in PVDF.

Figure 10:
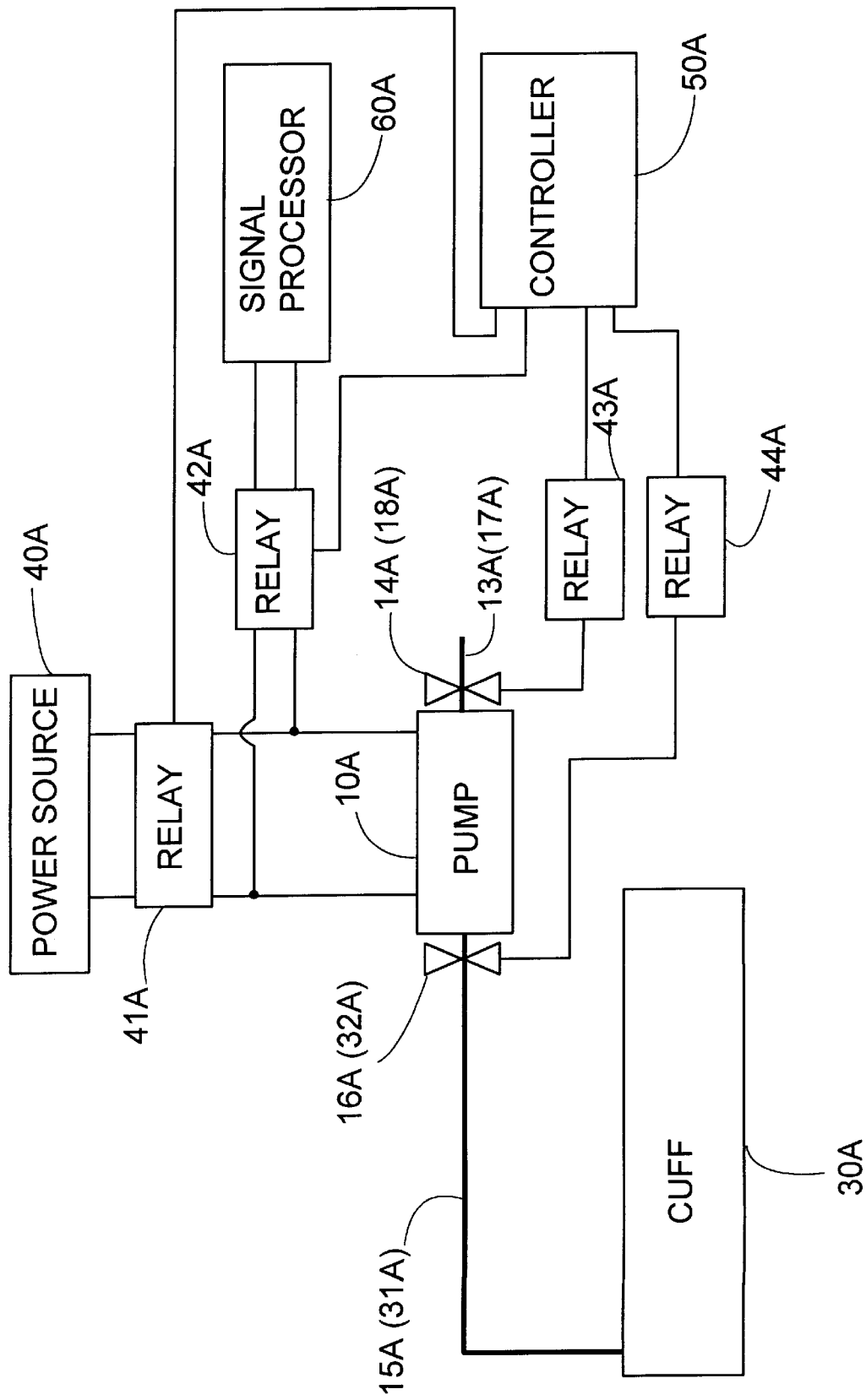
FIG. 10 is a block diagram of another pump system in accordance with a second embodiment of the present invention.

FIG. 10 illustrates an alternative pump system in accordance with a second embodiment of the present invention. The system is identical to the first embodiment except that a diaphragm pump 10A is equipped with an inlet valve 14A and an outlet valve 16A both of which are of active type rather than passive type. Like parts are designated by like numerals with a suffix letter of "A". The inlet and outlet valves 14A and 16A are controlled through individual relays 43A and 44A by a like controller 50A to draw in the outside air in the pump 10A and discharge it to the cuff 30A in synchronism with the actuation of the diaphragm. Inlet and outlet valves 14A and 16A are dual-purpose ones which act also as a release valve 18A and return valve 32A, respectively for evacuating the pump 10A and for introducing the pressurized air from the cuff 30A. In this consequence, an inlet path 13A from the pump also acts as a release path 17A, and an outlet path 15A as a return path 31A, whereby reducing a number of parts or elements in the system for simplifying the structure of the pump system. The measurement of the systolic and diastolic pressures can be made in the same manner as in the first embodiment.

Figure 11:
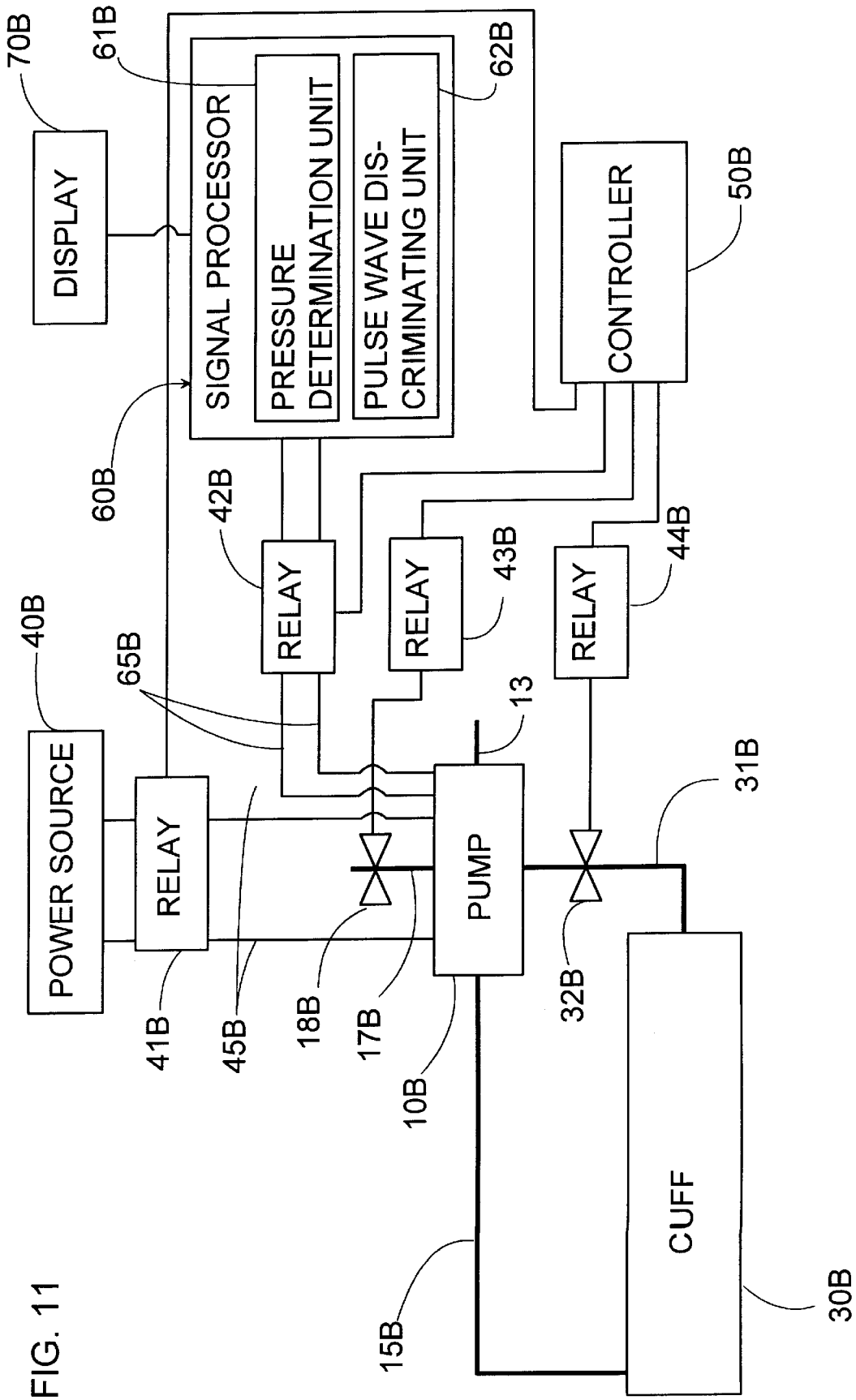
FIG. 11 is a block diagram of a further pump system in accordance with a third embodiment of the present invention.
Figure 12:
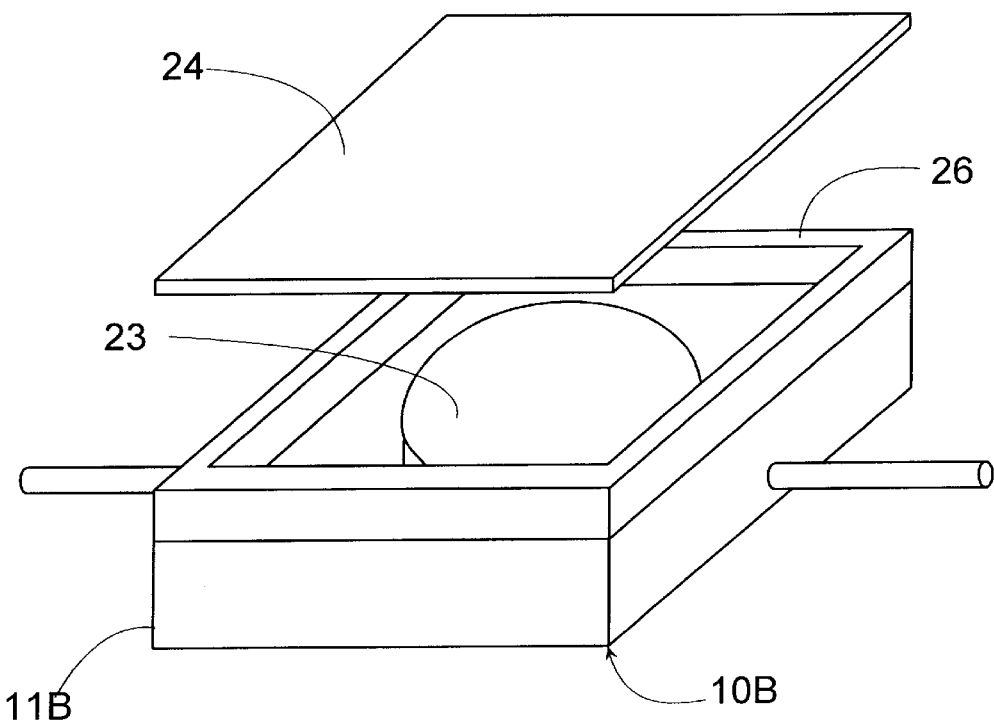
FIG. 12 is an exploded perspective view of a diaphragm pump for use in the pump system of the third embodiment.
Figure 13:
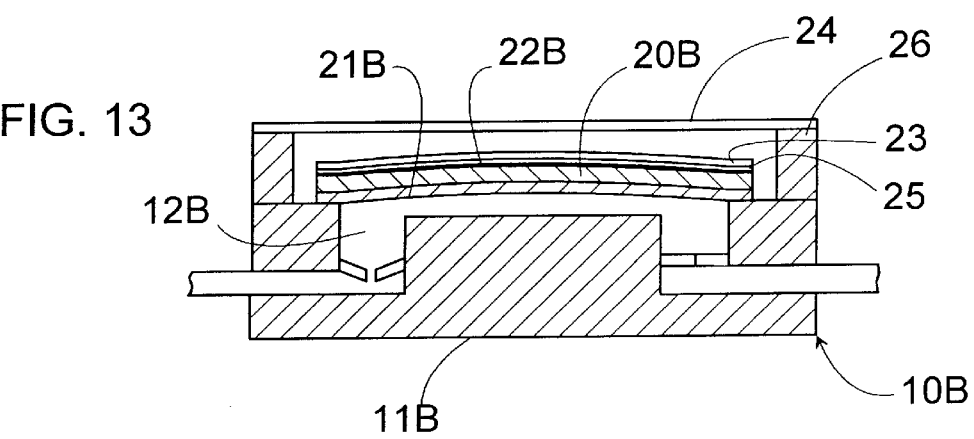
FIGS. 13 and 14 are sectional views illustrating an operation of the pump of FIG. 12.
Figure 14:
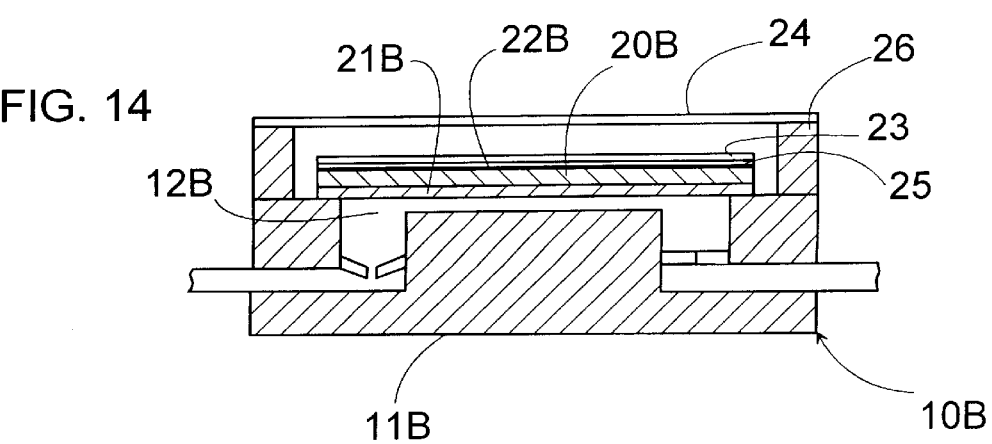

FIG. 11 illustrates a pump system in accordance with a third embodiment of the present invention which is similar to the first embodiment except for the use of a pump 10B which provides a sensor output derived from a varying static capacitance caused by the displacement of the diaphragm, rather than the voltage output from the diaphragm of piezoelectric element. Like parts and elements are designated by like numerals with a suffix letter of "B". As shown in FIGS. 12 to 14, the pump 10B includes a diaphragm 20B which is made of a PZT piezoelectric element and is additionally provided with a movable sensor electrode 23. The movable sensor electrode 23 is opposed to a fixed sensor electrode 24 to form a gap therebetween. As the diaphragm 20B deforms under the effect of the pressurized air introduced into the pump cavity 12B, the movable sensor electrode 23 is caused to move in a direction of varying a static capacitance in the gap, which variation is then derived as indicating the instant cuff pressure and is transmitted to a signal processor 60B for determination of the systolic and diastolic pressures in the same manner as in the first embodiment.

The movable sensor electrode 23 is formed over the entire upper surface of the diaphragm 20B with a dielectric layer 25 interposed therebetween. The fixed sensor electrode 24 is supported through a peripheral bridge 26 of a dielectric material to a periphery of a pump casing 11B. It is noted in this connection that the diaphragm 20B sandwiched between driving electrodes 21B and 22B is supported at its periphery to the pump casing 11B around a pump cavity 12B to have a center movable part responsible for pumping action and a peripheral stationary part connected to the pump casing. The dielectric layer 25 is deposited entirely over the top surface of the diaphragm of a planar configuration, then the movable sensor electrode 23 is deposited over the entire area of the dielectric layer 25.

With the use of the static capacitance for sensing the displacement of the diaphragm, the system is easy to monitor a minute pressure variation of the pressurized air introduced in the pump cavity for more accurate and reliable blood pressure determination, and is advantageous for digital processing of the electrical signal derived from the variation in the static capacitance.

Figure 15:
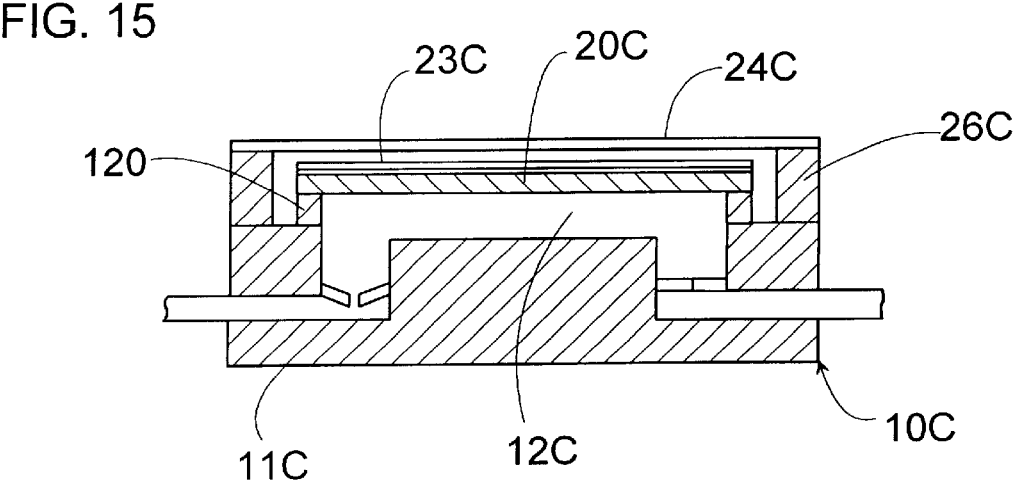
FIG. 15 is a sectional view illustrating a modification of the pump.

FIG. 15 shows a modified pump 10C which may be utilized in the above system. The pump 10C comprises a diaphragm 20C of rather rigid structure carrying at its periphery a piezoelectric actuator 120 of annular configuration by which the diaphragm is supported to the pump casing 11C around the pump cavity 12C. A movable sensor electrode 23C is deposited over the entire top face of the diaphragm 20C in an opposed relation to a fixed sensor electrode 24C which is fixed to the pump casing 11C by a peripheral bridge 26C. Upon being applied a DC pulse voltage, the piezoelectric actuator 120 deforms in the direction of oscillating the diaphragm substantially linearly for effecting the pumping action to inflate the cuff. When the diaphragm 20C is caused to displace by the pressurized air introduced into the pump cavity 12C in the absence of the DC pulse voltage, the movable sensor electrode 23C oscillating together with the diaphragm will vary a static capacitance across the two sensor electrodes 23C and 24C, thereby giving a corresponding electrical signal to the processor.

Figure 16:
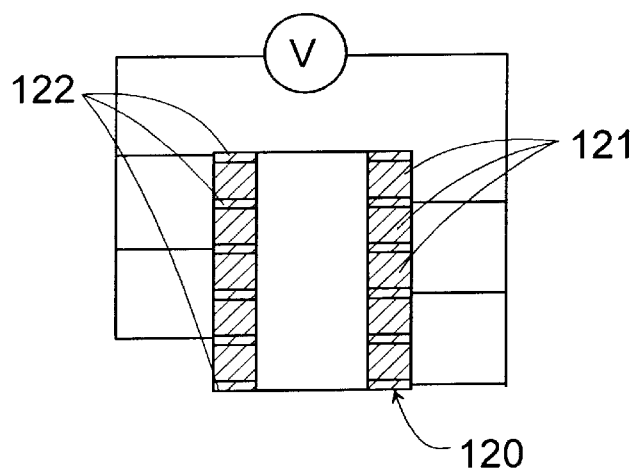
FIG. 16 is a schematic view of a piezoelectric element for driving the pump of FIG. 15.

As shown in FIG. 16, the piezoelectric actuator 120 is of a multilayer structure composed of layers 121 of a piezoelectric material with electrodes 122 interposed therebetween and disposed on the top and bottom of the structure. The layers 121 are connected in parallel with each other across the driving voltage source. The multi-layer structure is advantageous for increasing the amount of displacement of the diaphragm with a less voltage requirement.

Figure 17:
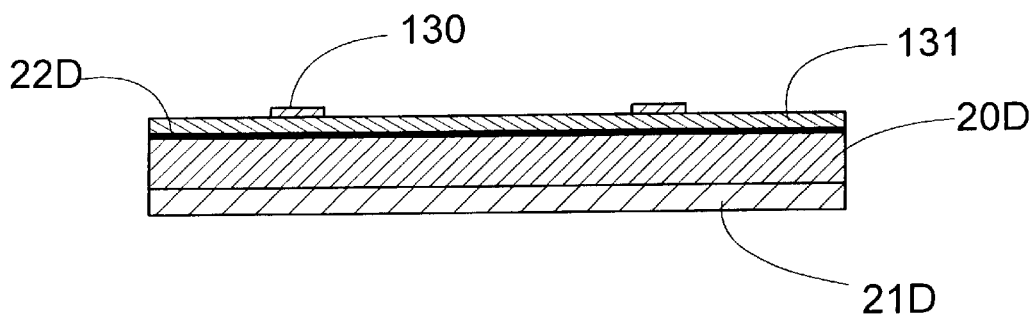
FIG. 17 is a sectional view of a diaphragm provided with a piezoelectric resistor network for use as an alternative to the first and second embodiments.

FIG. 17 shows a diaphragm 20D which is made of a PZT piezoelectric material and is provided with a piezoelectric resistor network 130 formed on top of the diaphragm with a dielectric layer 131 interposed therebetween. The network is composed of four piezoelectric resistors connected to form a bridge circuit which gives a varying resistance or voltage proportional to a strain or deformation applied to the diaphragm 20D. Driving electrodes 21D and 22D are formed on opposite faces of the diaphragm 20D. The variation of the resistance or voltage is monitored as indicative of the instant pressure of the pressurized air deforming the diaphragm for determination of the systolic and diastolic pressures in the same manner as in the first embodiment. The piezoelectric resistor may be either in the form of an additional patch or in the form of a buried segment in a thin film. In the latter form, resistor is preferred to be made from a material having a high gauge resistance such as chromium oxide, amorphous silicon, and polysilicon.

Figure 18:
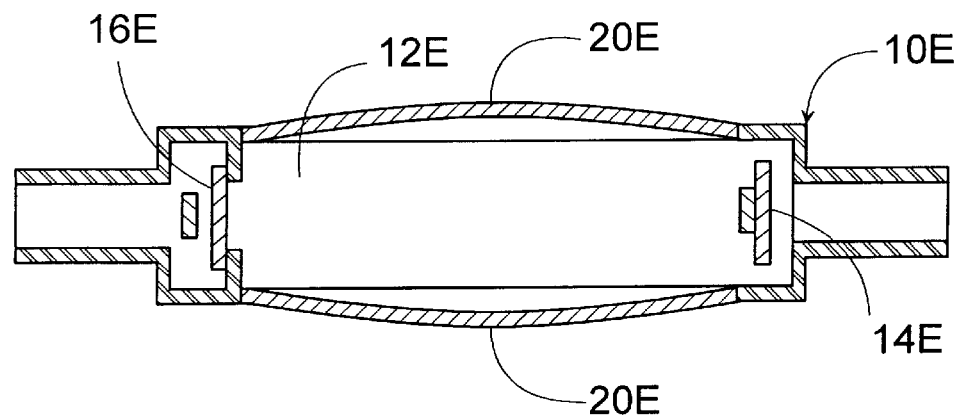
FIGS. 18 and 19 are vertical and horizontal sections of another diaphragm pump which may be utilized in the above pump systems.
Figure 19:
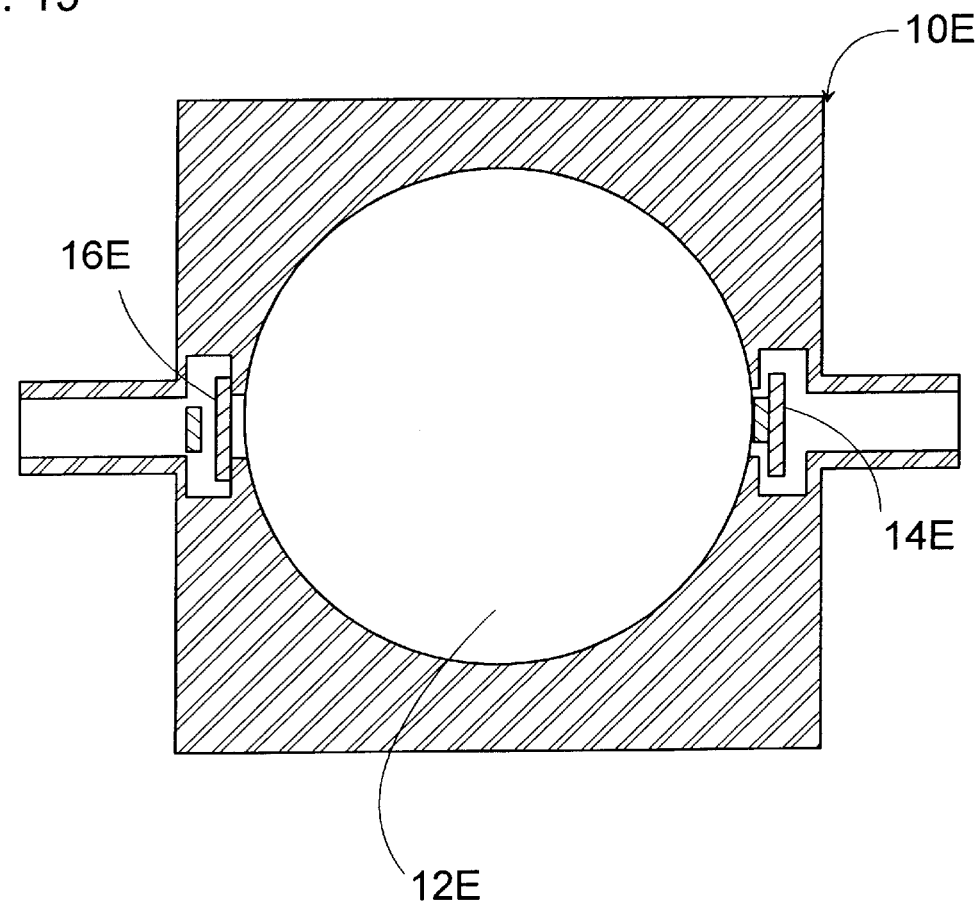

FIGS. 18 and 19 show a diaphragm pump 10E which may be utilized in the pump system of the present invention. The pump 10E is designed to increase a pumping capacity by provision of two piezoelectric diaphragms 20E on opposite of a flat pump cavity 12E. The diaphragms 20E are driven to displace outwardly simultaneously to draw in the outside air through an inlet valve 14E and then displace inwardly to discharge the air through an outlet valve 16E.

Figure 20:
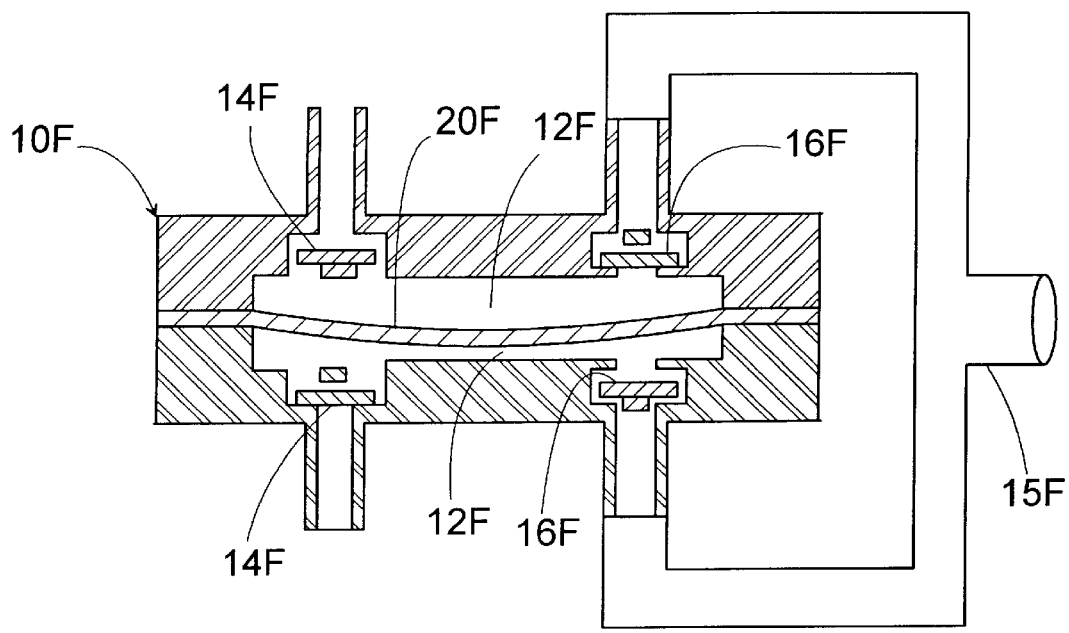
FIGS. 20 and 21 are vertical and horizontal sections of a further diaphragm pump which may be utilized in the above pump systems.
Figure 21:
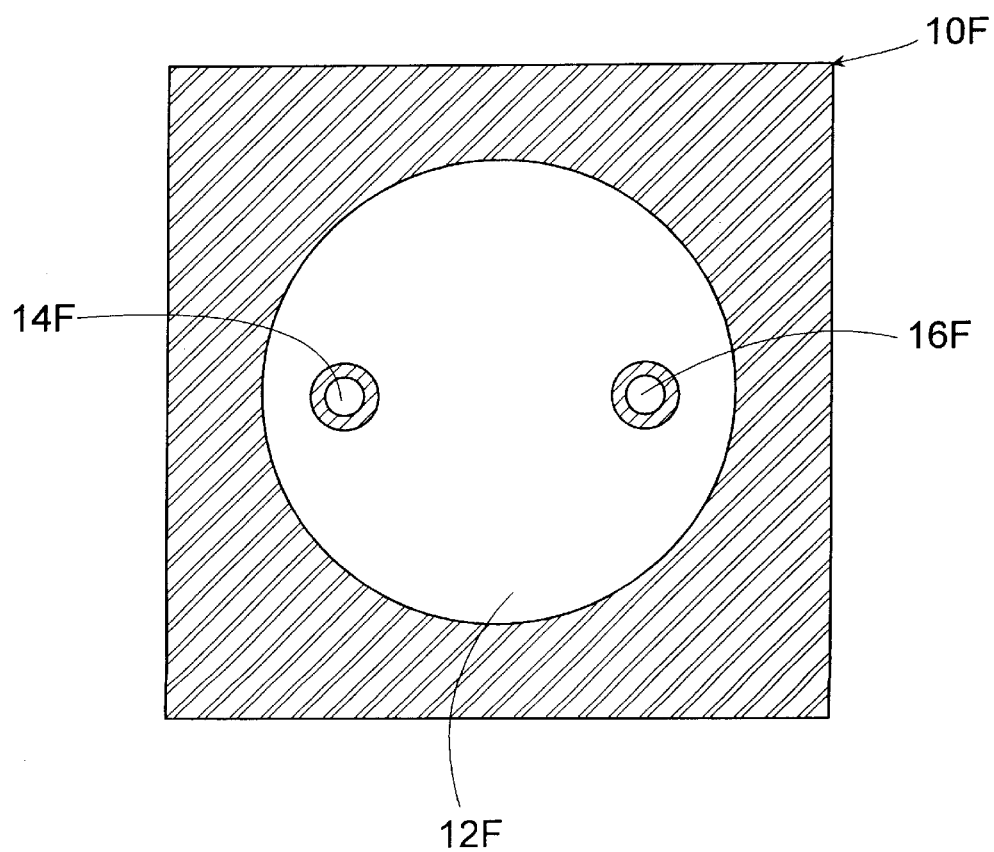

FIGS. 20 and 21 show another diaphragm pump 10F which may be equally utilized in the pump system of the present invention for the purpose of enhancing a pumping capacity. The pump 10F includes a single piezoelectric diaphragm 20F which divides a pump cavity into two sub chambers 12F each provided with an inlet valve 14F and an outlet valve 16F. The outlets of the two chambers 12F are joined into a single outlet path 15F for feeding the air to the cuff, thereby accumulating the pressurized air in the cuff efficiently with a small sized structure of the pump.

In the above illustrated embodiments, the pump system of the present invention is explained for pumping the air in the blood pressure measurement only by way of example. However, the system should not be limited to this specific use and can be utilized for handling a different fluid medium without substantially modifying the disclosure.

LIST OF REFERENCE NUMERALS

| | |
|---|---|
| 10 | pump |
| 11 | casing |
| 12 | pump cavity |
| 13 | inlet path |
| 14 | inlet valve |
| 15 | outlet path |
| 16 | outlet valve |
| 17 | release path |
| 18 | release valve |
| 20 | diaphragm |
| 21 | driving electrode |
| 22 | driving electrode |
| 23 | movable sensor electrode |
| 24 | fixed sensor electrode |
| 25 | dielectric layer |
| 26 | peripheral bridge |
| 30 | cuff |
| 31 | return path |
| 32 | return valve |
| 40 | power source |
| 41 | relay |
| 42 | relay |
| 43 | relay |
| 44 | relay |
| 45 | drive line |
| 50 | controller |
| 60 | signal processor |
| 61 | pressure determination unit |
| 62 | pulse wave discriminating unit |
| 65 | signal line |
| 70 | display |
| 120 | piezoelectric actuator |
| 121 | layer |
| 122 | electrode |
| 130 | piezoelectric resistor network |
| 131 | dielectric layer |

What is claimed is:

1. A method for measuring a pressure of a pressurized fluid fed through a diaphragm pump and accumulated in a vessel, said diaphragm pump having a pump cavity and a diaphragm with a piezoelectric element which is actuated by application of a voltage to displace said diaphragm for pumping a fluid into said vessel, said method comprising the steps of:

deenergizing said diaphragm by removal of the voltage to said piezoelectric element so as to stop pumping the fluid and accumulating the pressurized fluid into said vessel;

introducing said pressurized fluid only from said vessel back into said pump cavity so as to cause a displacement of said diaphragm by said pressurized fluid;

deriving an electrical signal indicative of the displacement of said diaphragm; and translating said electrical signal into a corresponding pressure value indicative of the pressure of said pressurized fluid in said vessel.

2. The method as set forth in claim 1, wherein said electrical signal is a voltage which is developed at said piezoelectric element as a result of the piezoelectric element being stressed by the displacement of said diaphragm under the effect of said pressurized fluid introduced into said pump cavity back from said vessel.

3. The method as set forth in claim 2, wherein said voltage is integrated over a predetermined time period to give an integrated voltage which is processed to into said pressure value.

4. The method as set forth in claim 1, wherein said electrical signal is based upon a static capacitance which is defined between a fixed sensor electrode and a movable sensor electrode on said diaphragm and which varies in response to the displacement of said diaphragm under the effect of said pressurized fluid introduced into said pump cavity back from said vessel.

5. The method as set forth in claim 1, wherein said electrical signal is given from a resistance of a piezoelectric resistor network which is disposed on said diaphragm to vary its resistance in response to the displacement of said diaphragm under the effect of said pressurized fluid introduced into said pump cavity back from said vessel.

6. A miniature pump system for accumulating a pressurized fluid into a vessel and having a capability of measuring the pressure of the pressurized fluid, said pump system comprising:

a pump having a pump cavity and a diaphragm covering said pump cavity, said diaphragm including a piezoelectric element which displaces the diaphragm, in response to a voltage applied to said piezoelectric element, to draw a fluid into the pump cavity and feed it into said vessel for accumulating said pressurized fluid in said vessel;

return means which allows said pressurized fluid to return into said pump cavity from said vessel while prohibiting non-pressurized fluid from entering said pump cavity;

control means which provides a measurement cycle and deenergizes, within said measurement cycle, said piezoelectric element to stop actuating the diaphragm while at the same time activates said return means to introduce the pressurized fluid into said pump cavity back from said vessel for displacing said diaphragm by the pressurized fluid being introduced; and processing means which derives an electrical signal caused by the displacement of said diaphragm within said measurement cycle and translate the electrical signal into a corresponding pressure value indicative of the pressure of said pressurized fluid in said vessel.

7. The system as set forth in claim 6, wherein said diaphragm is made of the piezoelectric element so as to generate a voltage as a result of being stressed by the displacement of the diaphragm within said measurement cycle, and said processing means deriving the voltage as said electrical signal for determination of the pressure value of said pressurized fluid.

8. The system as set forth in claim 7, wherein said piezoelectric element of said diaphragm has a composite structure composed of a first piezoelectric material and a second piezoelectric material mixed with said first piezoelectric material, and said first piezoelectric material having a piezoelectric strain constant (d33) greater than the second piezoelectric material, said first piezoelectric material having a voltage output constant (g33) smaller than said second piezoelectric material.

9. The system as set forth in claim 6, wherein said diaphragm carries a movable sensor electrode which displaces together with said diaphragm and is opposed to a fixed sensor electrode so as to vary a static capacitance between said movable and fixed sensor electrodes as said diaphragm is caused to displace within said measurement cycle, and said processing means deriving the static capacitance as said electrical signal for determination of the pressure value of said pressurized fluid.

10. The system as set forth in claim 9, wherein said diaphragm is of a planar configuration and is supported at its periphery to a casing of said pump around said pump cavity so as to have a center movable part responsible for pumping action and a peripheral stationary part connected to said casing, said movable sensor electrode extending over substantially the entire surface of one face of said diaphragm with a dielectric layer interposed therebetween, and said fixed sensor electrode being of a planar configuration and fixed to said casing so as to form a gap with said movable sensor electrode on said diaphragm.

11. The system as set forth in claim 9, wherein said diaphragm is of a planar configuration carrying at its periphery an annulus of said piezoelectric element by which said diaphragm is supported to a casing of said pump around said pump cavity, said piezoelectric element actuating to displace said diaphragm substantially linearly in a direction of varying a gap between said movable and fixed sensor electrodes while varying a volume of said pump cavity, said movable sensor electrode extending over substantially the entire surface of one face of said diaphragm, and said fixed sensor electrode being of a planar configuration and fixed to said casing.

12. The system as set forth in claim 11, wherein said piezoelectric element is of a multi-layer structure composed of layers of a piezoelectric material connected in parallel with each other across a driving voltage source.

13. The system as set forth in claim 6, wherein said diaphragm is formed on its surface with a piezoelectric resistor network which gives a varying resistance in response to the displacement of said diaphragm within said measurement cycle, said processing means deriving the resistance as said electrical signal for determination of the pressure value of said pressurized fluid.

14. The system as set forth in claim 13, wherein said piezoelectric resistor network is formed by being deposited on said diaphragm.

15. The system as set forth in claim 6, wherein said fluid is an air and said pump is provided with an active release valve which is capable of being actuated to open the pump cavity at an atmospheric pressure; and said control means actuating said release valve to open immediately before activating said return means to introduce the pressurized air into the pump cavity back from said vessel.

16. The system as set forth in claim 6, wherein said fluid is an air and said pump is provided with inlet and outlet valves respectively at an inlet of the pump for drawing the air and at an outlet of the pump for feeding the air into said vessel, and said inlet and outlet valves being of a microstructure having an valve opening of not more than 0.5 mm in diameter and operating at an opening/closing time of not more than 0.1 sec.

17. The system as set forth in claim 16, wherein each of said inlet and outlet valves is operatively connected to a piezoelectric actuator so as to be driven thereby to open and close.

18. The system as set forth in claim 6, wherein more than one said diaphragms surrounds the pump cavity.

19. The system as set forth in claim 6, wherein said diaphragm divides the pump cavity into two sub-chambers each provided with an inlet for drawing the fluid and an outlet for feeding the fluid into the vessel, and the two outlets of the sub-chambers joining with each other to feed the fluid from the sub-chambers into the vessel.

20. The system as set forth in claim 6, wherein said fluid is an air and said vessel is a cuff for occluding an artery of a human body, said processing means further including pulse wave discriminating means which monitors a pulse wave occurring in said pressurized air within said measurement cycle so as to detect an appearance of systole and diastole and provide systole and diastole signals respectively at the detection of said systole and diastole; and said processing means allocating said the pressure values to the systole and diastole signals for giving systolic and diastolic pressures.

* * * * *